United States Patent [19]

Southard

[11] Patent Number: 4,590,061

[45] Date of Patent: May 20, 1986

[54] ANTIMICROBIAL PLAQUE DISCLOSING AGENT

[75] Inventor: George L. Southard, Fort Collins, Colo.

[73] Assignee: Vipont Laboratories, Inc., Fort Collins, Colo.

[21] Appl. No.: 732,651

[22] Filed: May 10, 1985

Related U.S. Application Data

[63] Continuation-in-part of Ser. No. 566,916, Dec. 29, 1983, Pat. No. 4,517,172.

[51] Int. Cl.[4] .................. A61K 7/26; A61K 35/78
[52] U.S. Cl. ............................ 424/7.1; 424/49; 424/58; 424/195.1
[58] Field of Search .................. 424/7.1, 49, 58; 514/195.1

[56] References Cited

U.S. PATENT DOCUMENTS

| | | | |
|---|---|---|---|
| 209,331 | 10/1878 | Daniel | 424/195 |
| 2,344,830 | 3/1944 | Mohs | 424/195 |
| 3,309,274 | 3/1967 | Brilliant | 424/7.1 |
| 4,145,412 | 3/1979 | Ladanyi | 424/58 |
| 4,335,110 | 6/1982 | Collins | 424/58 |
| 4,406,881 | 9/1983 | Ladanyi | 424/49 |
| 4,517,172 | 5/1985 | Southard | 424/7.1 |

FOREIGN PATENT DOCUMENTS

| | | |
|---|---|---|
| 888843 | 11/1981 | Belgium . |
| 2907406 | 9/1980 | Fed. Rep. of Germany . |
| 2042336 | 9/1980 | United Kingdom . |

OTHER PUBLICATIONS

Hocking a Dictionary of Terms in Pharmacognosy Chas. C. Thomas Springfield, Ill. (1959), pp. 199–200, "Sanguinaria Canadensis".

Steinmetz Codex Vegetabilis (1977) Amsterdam Neth., #1018, "Sanguinaria Canadensis".

Windholz et al., Merck Index 9th ed. (1976) Merck & Co. Rahway, N.J., #8111, "Sanguinaria" #8112, Sanguinarine #2007, Chelerythrine #7684, Protupine.

*Primary Examiner*—Shep K. Rose
*Attorney, Agent, or Firm*—Eric P. Schellin

[57] ABSTRACT

Benzo-c-phenanthridine salts, either pure salts or salts precipitated form extracts of plants selected form the group consisting of *Sanguinaria canadensis, Macleaya cordata, Corydalis sevctvozii, C. ledebouni, Chelidonium majus,* and mixtures thereof, are effective agents for disclosing plaque in the oral cavity under long wavelength ultraviolet light.

12 Claims, No Drawings

ANTIMICROBIAL PLAQUE DISCLOSING AGENT

The present application is a continuation-in-part of Ser. No. 566,916, filed Dec. 29, 1983 entitled Plaque Disclosing Agent, now U.S. Pat. No. 4,517,172.

BACKGROUND OF THE INVENTION

The present invention relates to novel antimicrobial disclosing agents for use in the improvement of oral hygiene practice.

Dental plaque is a well-organized structure which forms on tooth surfaces and restorations. It consists mainly of bacteria surrounded by a matrix derived primarily from saliva and the bacteria themselves. Plaque differs from other soft tooth deposits such as material alba and food debris in that it has a definite architecture and cannot be flushed away by rinsing with water.

It is well established that dental plaque plays a major role in the etiology of periodontal disease and caries. Although the exact manner in which plaque contributes to these disease states is not known at present, it is appreciated that effective and thorough removal of these deposits is absolutely essential for control, and that a removal program must be established as part of the treatment plan for every dental patient. For this program to be effective, the patient must be motivated to carry out thorough daily plaque control techniques. Motivation can be achieved, however, only by establishing goals that are meaningful and attainable by the patient. Experience has shown that most patients would not be sufficiently motivated to practice good oral hygiene if they were simply told that plaque is a bacterial colony growing on their teeth, and that plaque produces gingival disease and caries and must be removed daily. However, the entire concept of what plaque is and what it does to tissue can be made vital and important to the patient by visualization, whereby every patient is shown his plaque in situ and under the phase contrast of a microscope. The patient may also observe the diseased gingival are as and their juxtaposition to the places of plaque accumulations. These visual demonstrations serve two main purposes. First, it shows the patient that he does indeed have these dangerous bacterial deposits called plaque on his teeth. Secondly, in the microscopic visualization, he sees that those innocent looking masses are composed of millions of living bacteria of differing shapes. Experience has shown that the technique of visualization of plaque generates in patients a true interest in plaque and an obvious and apparent concern for its prompt removal.

Recent evidence has shown that plaque has a great destructive potential and, under varying conditions, can cause gingivitis and periodontitis, produce dental caries, or form into calculus. It has also been established that plaque accumulation which is allowed to develop without removal in many cases may cause gingivitis within one to twenty one days. There is also recent evidence indicating that plaque with all of its components may be capable of producing an allergic response in adjacent soft tissues.

This rather substantial potential destructiveness has given rise to the increased attention and the resultant recent attempts to educate the public in the control of plaque. Generally, this control has adopted an approach of oral lavage and focused on the tasks such as brushing, stimulating, massaging, rinsing, spraying, and the like. However, while these techniques are effective for the removal of food debris and similar foreign matter, they are not very effective for removal of plaque. Plaque formation is transparent and is therefor not readily visible, particularly to one who is not skilled in its detection, and most often its removal occurs mainly by accident during oral lavage.

In order to increase the effectiveness of plaque detection and removal, there has been a recent introduction into the marketplace of staining compositions or so-called disclosing compositions. These disclosing compositions contain coloring agents or dyes which are designed to be absorbed by the plaque to make the plaque visually distinguishable form the remainder of the oral cavity. The active staining ingredient in most of these commercially available disclosing compositions is generally iodine or several organic dyes which serve as the primary diagnostic agent.

Organic dyes have been almost universally adopted for use in the commercially available disclosing compositions because of their higher degree of effectiveness. However, in almost all of these cases these dyes have a highly unpalatable and objectionable taste which is not effectively masked by any known flavoring agent or sweetner.

In order to obviate the need of disclosing solutions as a diagnostic device, there has been a recent introduction in the marketplace of fluoresecent light detection systems. These types of light detection systems rely upon compositions which are introduceable into the oral cavity and contain an ingredient which is fluorescent when activated by a proper light source. It is contended that the fluorescent ingredient or dye is absorbable by the plaque and that the fluorescent dye will only flouresce on the areas containing plaque formation when excited by the proper light source. However, in most cases the dye fluorsces at the same color as the enamel, and, therefore, the plaque is not readily distinguishable. Furthermore, the purchase cost for these systems generally have militated against their widespread use.

It has been found that benzo-c-phenanthridine alkaloids, which have antimicrobial properties, are also effective in disclosing plaque under long UV light. These compounds are of particular use in disclosing plaque because they also have a positive effect on the oral cavity and they are substantive to mouth tissue.

One of the important sources of the benzo-c-phenanthridine alkaloids is a perennial herb native to North Americla called *Sanguinaria candensis Linne* (Family: Papvaracea), commonly known as blood root, redroot, puccoon, and the like. The plant contains benzo-c-phenanthridine alkaloids including sanguinarine, chelerythrine, and several others. The maining benzo-c-phenanthridine alkaloids useful as antimicrobial agents are sanguinarine, sanguirubine, sanguilutine, chelerythrine, homochelidonene, chelirubine, protopine, and mixtures thereof.

The pure chemicals sanguinarine, cherlerytherine, and other benzo-c-phenanthridine alkaloids can be isolated form other plants besides Sanguinaria. Also, they are available, although rarely, form some chemical supply houses. Semi-purified forms of the alkaloids are commercially available, and these are generally referred to as sanguinarine nitrate and sanguinarine sulfate. These "salts" are the salts of the mixed alkaloids of the plant Sanguinaria: mainly sanguinarine, chelerythrine, and protopine. While few references can be found in the literature regarding the usage of any of the pure benzo-c-phenanthridine alkaloids, plants containing such compounds have been used for medical purposes for quite some time for a wide variety of ailments.

An early U.S. Pat. No. 209,331, discloses the use of bloodroot, zinc chloride, and kerosene oil in equal proportions for treating open sores. U.S. Pat. No. 433,257 describes a salve of pulverized bloodroot, armenian bole, powdered rosin, lard, and Stockholm tar for use in the treatment of piles. U.S. Pat. No. 2,344,830, discloses the use of a mixture of zinc chloride, stibnite, and bloodroot, to fix and outline diseased tissue for excision by surgery.

Several more recent patents have disclosed the use of extracts of Sanguinaria for treating the oral cavity for conditioning oral tissue as well as in preventing and treating gingivitis, periodontitis, and mouth odors. Some of the patents describing the use of sanguinaria extracts as antimicrobial agents are U.S. Pat. No. 4,145,412; U.S. Pat. No. 4,406,881; U.K. Pat. No. 2,042,336; U.S. Pat. No. 4,376,115; German Offen. No. 2,907,406; Belgina No. 888,843. The use of sanguinarine with thiophosphoric acid for treating various human and animal neoplasms is shown in French Pat. Nos. 70-22029 and 2,152,972.

The benzo-c-phenanthridine alkaloids have been shown to have some antifungal and antiprotozoan properties. The antibacterial activity of benzo-c-phenanthridine alkaloids has been found to vary with the attached radicals, and various salts of the benzo-c-phenanthridine alkaloids have been found to have some activity against certain bacteria at various concentrations. Sanguinarine nitrate has been reported to have some weak bacteriostatic action on various types of bacteria.

SUMMARY OF THE INVENTION

It has been found that salts of the benzo-c-phenanthridine alkaloids disclose plaque equally as well as two standard disclosing agents, erythrosine and fluorescein. However, the benzo-c-phenanthridine alkaloids have been found to be retained on the plaque deposits for a significantly longer time than the standard disclosing agents, and the benzo-c-phenanthridine alkaloids are known to have antimicrobial properties.

The longer retention time for benzo-c-phenanthridine alkaloids on plaque deposits makes them ideal disclosants for use in dental offices, by allowing dental cleanings during the disclosure period while maintaining an antibacterial action on plaque and other tooth deposits. The antibacterial action of the benzo-c-phenanthridine alkaloids is particularly important in the case of ultrasonic scaling, where aerialization of mouth deposits is an occupational hazard to dentists and dental hygienists. Compositions containing benzo-c-phenanthridine salts as a disclosing agent can also be used by consumers for self-disclosure of plaque in the home to aid in oral hygiene.

The benzo-c-phenanthridine alkaloid may be incorporated into a disclosing composition in a variety of ways. The most common method is to incorporate the benzo-c-phenanthridine salt into a mouthwash composition, which is used to rinse the mouth prior to examining it for plaque deposits. Alternatively, the salt may be incorporated into a test cracker or other chewable food such as candy or gum which will aid in diagnosing plaque. The salt can also be incorporated into toothpaste to enable the patient to observe the care with which he brushes.

In formulating preparations suitable for the above, one may include, if desired, one or more additives which are useful for other purposes. For example, brightening agents, solvents, spreading, or wetting agents, etc., may be used for various purposes. Almost any known mouthwash, toothpaste, tooth powder, or other formulation useful for diagnostic or therapeutic treatment of external body surfaces and of the oral cavity may be used.

Sanguinarine chloride was compared to two standard disclosing dyes, erythrosine and sodium fluorescein. At weekly interval healthy volunteers underwent a 12-24 hour, no oral hygiene period. Subjects then used one of the following: erythrosine, sodium flourescein, or sanguinarine chloride. Subjects rinsed two times with 15 ml. of the rinse, while the erythrosine and sodium fluorescein were used according to customary practice. Color was evaluated under ambient light after erythrosine, under ambient light for sodium fluorescein, and under longwave UV fluorescent light for sanguinarine. The color was scored for location, amount, and area.

All of the disclosing agents colored soft dental deposits at gingival margins and at the dorsal surface of the tongue. Erythrosine also stained the ginginvae and other soft tissues, whereas sodium fluorescein and sanguinarine did not. Mean values of plaque were measured for all disclosants. Table I shows that the sanguinarine chloride mouthwash disclosed plaque effectively, and that the disclosure lasted significantly longer than for the other two disclosing dyes.

TABLE I

| | Visual Assessment | |
|---|---|---|
| | Mean Plaque Area Score | |
| Active Agent | Baseline | 1 Hour later |
| Erythrosine | 2.86 + 0.43 | 2.18 + 0.5 |
| Sodium Fluorescein | 2.84 + 0.22 | 1.74 + 0.45 |
| Sanguinarine chloride | 2.87 + 0.23 | 2.86 + 0.26 |

Quantitative evaluation of sanguinarine in plaque and saliva by means of high performance liquid chromatography demonstrated levels in plaque much higher in vitro minimum inhibitory concentrations, as shown in TABLE II.

TABLE II

| In Vivo Plaque Retention of Sanguinarine (ug/g of wet plaque) | | | | | | |
|---|---|---|---|---|---|---|
| | Sample Time, Minutes | | | | | |
| Subject | 15 | 30 | 45 | 60 | 90 | 120 |
| 1 | 26 | — | 22 | — | 26 | — |
| 1A | 110 | — | 27 | — | 20 | — |
| 2 | 29 | — | 27 | — | 31 | — |
| 2A | 79 | — | 56 | — | 46 | — |
| 3 | 111 | — | 37 | — | 36 | — |
| 3A | 160 | — | 34 | — | 36 | — |
| 4 | — | 96 | — | 56 | 51 | — |
| 5 | — | 46 | — | 46 | 46 | 27 |

Levels of sanguinarine in saliva, as shown in Table III, were high enough to exert an anti-glycolytic effect on saliva. This would indicate that the retention of sanguinarine in plaque may be responsible for its clinical effectiveness in plaque assays, and that plaque may serve as a reservoir for sanguinarine.

TABLE III

| In Vivo Saliva Retention of Sanguinarine (ug/ml of saliva) | | |
|---|---|---|
| | Sample time, Minutes | |
| Subject | 15 | 45 | 60 |
| 6 | 1.13 | 0.92 | 0.45 |
| 7 | 1.47 | 0.75 | 0.60 |

TABLE III-continued

In Vivo Saliva Retention of Sanguinarine (ug/ml of saliva)

| Subject | Sample time, Minutes | | |
|---|---|---|---|
| | 15 | 45 | 60 |
| 26 | 1.96 | 0.79 | 1.00 |
| 20 | 0.80 | 0.57 | 0.42 |
| 27 | 0.90 | 0.90 | 0.80 |
| 21 | 0.47 | 0.17 | 0.22 |
| 28 | 2.63 | 1.25 | 0.54 |
| 22 | 0.50 | 0.29 | 0.18 |
| 24 | 1.05 | 0.85 | 0.80 |

The approximate retention times in oral tissues of six alkaloids found in extracts from Sanguinaria canadensis is shown in Table IV.

TABLE IV

| Alkaloid | Approximate Retention time, minutes |
|---|---|
| Chelirubine | 7.5 |
| Sanguinarine | 9.5–10.0 |
| Sanguirubine | 12.5–13.0 |
| Chelilutine | 15.5–16.0 |
| Chelerythrine | 16.5–17.0 |
| Sanguilutine | 18.5–19.0 |

DESCRIPTION OF THE PREFERRED EMBODIMENTS

The benzo-c-phenanthridine salts have been found to be useful in controlling dental plaque, as disclosed in abandoned application Ser. No. 468,751, filed Feb. 22, 1983, which disclosure is incorporated herein by reference. The benzo-c-phenanthridine salts which have been found to be useful in plaque disclosing agents include the chloride, the nitrate, and the sulfate salts of the benzo-c-phenanthridine alkaloids. The salts may be present in their pure form or as mixtures, such as those precipitated form extracts of *Sanguinaria candensis, Macleaya cordata, Carydali sevctocozii, C. ledebouni, Chelidonium majusm,* and other members of the Papaveracease.

EXAMPLE I

An oral rinse was formulated for use as a disclosing agent. The rinse contained the following ingredients:

| Sodium nitrate | 10.0 weight per cent |
|---|---|
| Sanguinarine chloride, 10% | 5.00 |
| Flavoring (oil of cinnamon) | 0.25 |
| Tween 80 | 0.60 |
| Deionized water | 83.95 |
| Pluronic F127 | 0.10 |
| Sodium saccharin | 0.10 |

This was the oral rinse used for the tests described in Tables I, II, and III.

EXAMPLE II

An oral rinse is formulated for use as a disclosing agent substituting 10.00% of mixed salts precipitated form *Sanguinaria canadensis* for the sanguinarine chloride above. This oral rinse, when used in a quantity of about 15 ml. for 15 seconds in the mouth gave acceptable plaque disclosure in the mouth under long wavelength ultraviolet light.

Oral rinses for use as plaque disclosing agents can incorporate from 0.010 to 0.50% pure benzo-c-phenanthridine salt (chloride, nitrate, sulfate, or other nontoxic salt), or from about 0.010 to about 0.50% mixed benzophenanthridine alkaloids.

The oral rinse compositions which have been found useful for the practice of the present invention generally comprise a water/ethyl alcohol solution and, optionally, other ingredients such as flavors, sweetners, and humectants. The rinse may also contain sudsing agents to aid in the penetration of the plaque. The sudsing agent is generally present in amounts of about 0 to about 12% by weight, with optional flavoring and coloring agents.

Suitable sudsing agents are those which are reasonably stable and form suds throughout a wide pH range, i.e., nonsoap nonionic, cationic, and amphoteric synthetic organic detergents.

The nonionic synthetic detergents which can be used with the oral rinse compositions of the present invention may be broadly defined as compounds produced by the condensation of a hydrophilic alkylene oxide group with an organic hydrophobic compound which may be aliphatic or aromatic in nature. The length of the hydrophilic or polyoxyalkylene racidal which is condensed with any particular hydrophobic group can be readily adjusted to yield a water-soluble compound having the desired degree of balance between hydrophilic and hydrophobic elements.

Cationic systhetic detergents useful in the mouthwash compositions of the present intention can be broadly defined as quaternary ammonium compounds having one long alkyl chain containing from about 8 to about 18 carbons, such as lauryltrimethylammonium chloride, cetyl pyridinium chloride, cetyltrimethylammonium bromide, di-isobutylphenoxyethyldimethylbenzylammonium chloride, cocoalkyltrimethylammonium nitrite, cetyl pyridinium fluoride, and the like.

The amphoteric synthetic detergents useful in the present invention can be broadly described as derivatives of aliphatic secondary and tertiary amines in which the aliphatic radical can be straight or branched and wherein one of the alkphatic substituents contains from about 8 to about 18 carbon atoms and one contains an anionic water water solubilizing group, such as carboxylate, sulfonate, phosphate, or phosphonate.

The oral rinse for use as a disclosing agent can also contain flavoring agents such as wintergreen oil, oil of peppermint, oil of sassafras, and oil of anise. Flavoring agents may be present at levels of from about 0.01% to about 2% by weight.

The disclosing compositions of the present invention may also be incorporated in pastes or powders that are topically applied, or in the form of chewable foodstuffs that can be chewed by the patient to apply the disclosing composition.

EXAMPLE III

A toothpaste is made by mixing together the following ingredients in the indicated proportions:

| Insoluble sodium methaphosphate | 26.60% |
|---|---|
| Dicalcuim phosphate | 26.60% |
| Gum | 1.40% |
| Flavoring | 1.60% |
| Sodium lauryl sulfate | 1.10% |
| Glycerol (40.7) and water (1.0%) | 41.70% |
| Sanguinarine sulfate | 1.00% |

The patient's teeth are brushed with this paste, and then exposed to longwave UV light. The plaque on teeth stands out in bold relief as compared to the adjacent clean and healthy areas.

EXAMPLE IV

A tooth powder is made by mixing together the following ingredients, in the indicated proportions:

| | |
|---|---|
| Microcrystalline aluminum hydroxide | 91.25% |
| Aluminum hydroxide (325 mesh) | 5.00% |
| Flavoring matter | 0.60% |
| Saccharin, soluble | 0.25% |
| Sodium fluoride | 0.10% |
| Sodium lauryl sulfoacetate | 2.30% |
| Chelerythrine chloride | 0.25% |
| Sanguinarine nitrate | 0.50% |

The benzo-c-phenanthridine salts can also be incorporated in chewable foods such as gum, gels, candies, or crackers which can be chewed by a patient to apply the the benzo-c-phenanthridine salts to the teeth to disclose plaque.

The benzo-c-phenanthridine salts can be incorporated into antimicrobial agents for treating teeth and gums which can also be used as disclosing agents for disclosing plaque.

The pure benzo-c-phenanthridine alkaloid is dissolved either in deinized water or $C_1$-$C_6$ alcohol, glycerine, propylene glycol, petrolatum, or other nontoxic organic solvents are 70 degrees C. The preparations generally contain from 0.10% to about 10.0% by weight of the benzo-c-phenanthridine alkaloid salt. The material can be diluted with the solvents listed above, or it can be incorporated into toothpaste, mouthwash, and the like as described above.

Sanguinarine chloride, as well as the other benzo-c-phenanthridine alkaloids, has been shown to have strong antimicrobial properties. The mean activating dose of sanguinarine chloride against a variety of microorganism is shown in Table V.

TABLE V

| Microorganism | Mean Inhibiting dose of sanguinarine chloride in ug/ml of media |
|---|---|
| Bacillus subtilis | 22 |
| Escherichia coli | 270 |
| Proteus vulgaris | 590 |
| Staphylococcus aureus | 70 |
| Streptococcus faecalis | 393 |
| Candida albicans | 150 |
| Saccharomyces cerevisiae | 20 |
| Pseudomonas aeruginosa | 7000 |
| Microsporum canis | 867 |
| Microsporum nanum | 650 |
| Trichophyton metagrophytes | 900 |
| Trichophyton terrestre | 467 |
| Trichophyton vanbreuseghemi | 750 |

It was further found that a concentration of sanguinarine chloride of 25 micrograms per milliliter caused a 100% reduction of dental plaque by inactivating plaque forming microorganisms freshly collected form human dental plaque forming microorganisms freshly collected form human dental plaque. Sanguinarine chloride compated favorably in vitro with chlorhexidine (Hibitane(R), a material used as a standard in evaluating inhibition of human dental plaque forming microorganisms.

What is claimed is:

1. A method for visualizing plaque formation in the oral cavity and rendering such plaque formation visible to the naked eye under long wavelength ultraviolet light without employing fluorescent or other disclosing dyes or stains by first applying to the teeth, with plaque formation, in the oral cavity a non-toxic benzo-c-phenanthridine salt and then exposing the teeth to longwave UV light, in order to thereby disclose the plaque on the teeth.

2. The method of claim 1 wherein the benzo-c-phenanthridine salt is selected form the group consisting of non-toxic salts of sanguinarine, sanguilutine, sanguirubine, chelerythrine, chelilutine, protopine, hemochelidinonene, and mixtures of salts from extracts of plants selected form the group consisting of *Sanguinaria canadensis, Macleaya cordata, Corydalis sevctvozii, C. ledebouni, Chelidonium majus,* and mixtures thereof.

3. The method of claim 2 wherein the salt is sanguinarine chloride.

4. The method of claim 2 wherein the salt is a mixture of sanguinarine chloride and chelerythrine chloride.

5. The method of claim 1 wherein the benzo-c-phenanthridine salt is contained in an oral rinse.

6. The method of claim 1 wherein the salt is a mixture of benzo-c-phenanthridine salts extracted form *Sanguinaria canadensis.*

7. The method of claim 1 wherein the benzo-c-phenanthridine salt is applied in the form of a toothpaste.

8. The method of claim 7 wherein the salt is sanguinarine chloride.

9. The method of claim 7 wherein the salt is a mixture of sanguinarine chloride and chelerythrine chloride.

10. The method of claim 1 wherein the benzo-c-phenanthridine salt is applied in the form of a tooth powder.

11. The method of claim 11 wherein the salt is sanguinarine chloride.

12. The method of claim 11 wherein the salt is a mixture of sanguinarine chloride and chelerythrine chloride.

* * * * *